(12) United States Patent
Zhang et al.

(10) Patent No.: US 10,541,048 B2
(45) Date of Patent: Jan. 21, 2020

(54) SYSTEM FOR MONITORING AND VISUALIZING A PATIENT TREATMENT PROCESS

(75) Inventors: Hongxuan Zhang, Palatine, IL (US); Dennis Steibel, Jr., Lake Zurich, IL (US)

(73) Assignee: Siemens Healthcare GmbH, Erlangen (DE)

( * ) Notice: Subject to any disclaimer, the term of this patent is extended or adjusted under 35 U.S.C. 154(b) by 1294 days.

(21) Appl. No.: 12/940,067

(22) Filed: Nov. 5, 2010

(65) Prior Publication Data

US 2011/0201900 A1    Aug. 18, 2011

Related U.S. Application Data

(60) Provisional application No. 61/305,676, filed on Feb. 18, 2010.

(51) Int. Cl.
*G16H 15/00* (2018.01)
(52) U.S. Cl.
CPC .................... *G16H 15/00* (2018.01)
(58) Field of Classification Search
CPC ........ G06Q 10/00; G06Q 50/00; G16H 10/00; G16H 10/40; G16H 15/00; G16H 20/00; G16H 20/10; G16H 20/13; G16H 20/17; G16H 30/00; G16H 40/00; G16H 50/00; G16H 70/00; G16H 80/00
USPC .................................................. 705/2, 3, 20
See application file for complete search history.

(56) References Cited

U.S. PATENT DOCUMENTS

| | | |
|---|---|---|
| 6,008,808 A | 12/1999 | Almeida |
| 6,075,530 A | 6/2000 | Lucas et al. |
| 6,381,576 B1 * | 4/2002 | Gilbert .............................. 705/2 |
| 6,416,471 B1 | 7/2002 | Kumar et al. |
| 6,473,638 B2 | 10/2002 | Ferek-Petric |
| 6,529,900 B1 | 3/2003 | Patterson et al. |
| 6,542,902 B2 | 4/2003 | Dulong et al. |
| 6,701,294 B1 | 3/2004 | Ball et al. |
| 6,751,630 B1 | 6/2004 | Franks et al. |
| 6,785,674 B2 | 8/2004 | Vu |
| 6,805,667 B2 | 10/2004 | Christopherson et al. |
| 6,931,288 B1 | 8/2005 | Lee et al. |
| 7,050,611 B2 | 5/2006 | Bodicker et al. |
| 7,051,012 B2 | 5/2006 | Cole et al. |

(Continued)

*Primary Examiner* — Robert W Morgan
*Assistant Examiner* — Charles P Coleman (57) ABSTRACT

A patient treatment monitoring system includes an interface for receiving multiple different types of patient medical information including data derived from a patient monitoring device and a patient medical imaging device. A data processor processes the received multiple different types of patient medical information to be suitable for presentation in a display image. A display processor initiates generation of data representing a single composite display image including an image element representing multiple sequentially performed individual stages of a treatment process. The individual stages are associated with corresponding different sets of the received multiple different types of patient medical information. The single composite display image includes multiple image areas for displaying one of the corresponding different sets of the received multiple different types of patient medical information, in response to user selection of a particular stage of the individual stages using the image element.

21 Claims, 8 Drawing Sheets

(56) References Cited

U.S. PATENT DOCUMENTS

| | | | |
|---|---|---|---|
| 7,218,968 B2 | 5/2007 | Condie et al. | |
| 7,343,305 B2 | 3/2008 | Benn et al. | |
| 7,371,068 B2 | 5/2008 | Lloyd et al. | |
| 7,384,267 B1 | 6/2008 | Franks et al. | |
| 7,433,827 B2 | 10/2008 | Rosenfeld et al. | |
| 7,434,226 B2 | 10/2008 | Singh | |
| 7,438,216 B2 | 10/2008 | Ambekar et al. | |
| 7,461,079 B2 | 12/2008 | Walker et al. | |
| 7,490,085 B2 | 2/2009 | Walker et al. | |
| 7,562,026 B2 | 7/2009 | Delmonego et al. | |
| 7,577,573 B2 | 8/2009 | Janas et al. | |
| 7,607,571 B2 | 10/2009 | Steusloff et al. | |
| 7,613,620 B2 | 11/2009 | Salwan | |
| 7,613,672 B2 | 11/2009 | West et al. | |
| 7,627,857 B2 | 12/2009 | Rokosz | |
| 7,640,172 B2 | 12/2009 | Kuth | |
| 7,756,727 B1 * | 7/2010 | Greenspan et al. | 705/3 |
| 2002/0082865 A1 * | 6/2002 | Bianco et al. | 705/2 |
| 2004/0267570 A1 * | 12/2004 | Becker | 705/2 |
| 2006/0085223 A1 * | 4/2006 | Anderson et al. | 705/2 |
| 2007/0118054 A1 * | 5/2007 | Pinhas et al. | 600/587 |
| 2008/0065424 A1 * | 3/2008 | Frick | 705/3 |
| 2009/0276700 A1 * | 11/2009 | Anderson et al. | 715/700 |
| 2010/0172567 A1 * | 7/2010 | Prokoski | 382/132 |
| 2010/0305973 A1 * | 12/2010 | McLaren et al. | 705/3 |

\* cited by examiner

| Function modules in workflow chain evidence tracking and evaluation | Function descriptions |
|---|---|
| Patient information | Including patient registration and automatic calculation system, such as age based NIBP range, etc |
| Patient history | Patient data on disease, family, medicine, treatment, etc |
| Patient status | Patient real time health status, such as scores, doctors' comments |
| Alarm and evaluation | Any abnormality warning, including patient status, system status (SW/HW), Lab status, etc |
| ECG/EP signals | Including surface ECG, intra-cardiac electrograms, etc |
| Hemo signals | Invasive and non-invasive blood pressures, stroke volume, and any blood related measurements and signals |
| Vital signs signals | Including respiration, SPO2, temperature, NIBP, etc |
| Event logs | Patient and procedure records, such as operation, treatment, etc |
| Images | Including X-Ray, ultrasound, fMRI, etc, this may be real time or non real time acquisition and data transmission (such as image and movies) |
| Medicines and drugs | Treatment history and records |
| User define module | Medical user defined application and important functions |
| Analysis and algorithms | Any user calculation, computation and diagnosis which may help to quantify and characterize the events, pathologies, such as 3-D mapping, EP functions real time mapping, etc |
| Visualization methods | Display and video visualization methods, such as multi-screen and multi-displaying in one screen, etc |
| Multi-cases comparison (real time | Including real time, non real time, cases |

SYSTEM FOR MONITORING AND VISUALIZING A PATIENT TREATMENT PROCESS

This is a non-provisional application of provisional application Ser. No. 61/305,676 filed Feb. 18, 2010, by H. Zhang et al.

FIELD OF THE INVENTION

This invention concerns a system for monitoring patient treatment including stages of a treatment process and displaying treatment related information from a patient monitoring device and a patient medical imaging device.

BACKGROUND OF THE INVENTION

Medical systems record, monitor and diagnose many kinds of patient data, such as patient medical history information, vital sign signals (ECG (electrocardiograms), ICEG (intra-cardiac electrocardiogram), MEW (non-invasive blood pressure), SPO2 (blood oxygen saturation), respiration, temperature, signals), waveforms, calculation results and diagnosis, drug delivery, event logs information, medical images. Different medical devices may use different ways to present information such as in text logs, via graphics, images, voice recordings, including real time patient signals and status data. However, different systems from different companies use different user interfaces to display and track medical patient data and procedures. Known clinical application systems are often subjective and need extensive expertise and clinical experience for accurate patient data interpretation. There is also a lack of a comprehensive standard for medical information display.

Known medical devices typically fail to integrate and combine medical information (from a patient, doctor, nurse, patient setting, drug applications, diagnoses, for example) and to present the information to clinical users in a user friendly manner. Known patient monitoring devices collect, different kinds of signals, data and information, such as ECG, ICEG, blood pressure, NIBP, SPO2, image, drug delivery and system changes. However known systems lack standard data processing and presentation methods and processing depends on individual medical user preference, which requires extensive knowledge and experience of application software (SW) and hardware (HW) and are vulnerable to subjective disparate interpretation by different users. Known systems fail to efficiently combine, synchronize and control different types of data, signals and images used in clinical application. Known systems also lack user friendly operation facilitating user improvement of workflow and clinical applications and fail to adequately categorize medical information, data and diagnoses allocating appropriate priority for physician evaluation. A system according to invention principles addresses these deficiencies and related problems.

SUMMARY OF THE INVENTION

A system improves accuracy and reliability of cardiac procedure monitoring and diagnosis, and provides a user friendly UI interface, that integrates and combines different kinds of clinical information (such as patient, environment, drugs, diagnosis information) to improve monitoring real time clinical data during a procedure and to improve data interpretation during a clinical procedure. A patient treatment monitoring system includes an interface for receiving multiple different types of patient medical information including data derived from a patient monitoring device and a patient medical imaging device. A data processor processes the received multiple different types of patient medical information to be suitable for presentation in a display image. A display processor initiates generation of data representing a single composite display image including an image element representing multiple sequentially performed individual stages of a treatment process. The individual stages are associated with corresponding different sets of the received multiple different types of patient medical information. The single composite display image includes multiple image areas for displaying one of the corresponding different sets of the received multiple different types of patient medical information, in response to user selection of a particular stage of the individual stages using the image element.

DETAILED DESCRIPTION OF THE INVENTION

A system improves accuracy and reliability of cardiac procedure monitoring and provides a user friendly interface that integrates presentation of different kinds of clinical information (such as patient, environment, drug and diagnosis information) in providing an evidence based medical data viewing system for use in a clinical workflow. The system employs medical guidelines to improve a user interface for viewing patient data to improve monitoring during a clinical procedure and to improve data interpretation during the clinical procedure. The system identifies cardiac disorders, differentiates between cardiac arrhythmias, characterizes pathological severity, predicts life-threatening events and evaluates drug delivery effects.

Medical system configuration information including system self test information is advantageously presented to a user. The medical system configuration data may be changed due to procedure needs, such as for ablation, stimulation, defibrillation. The system configuration and configuration update data, (e.g. of an imaging system, vital sign system, patient data sampling system, treatment system), is presented together with clinical data. The system records patient information in a log and monitors ongoing patient signals to provide real time characterization and interpretation of patient signals, data and images and provides online evaluation of clinical data and patient health status. The system provides clinical procedure evaluation using an evidence based scoring method as well as retrospective case diagnosis and comparison of multiple medical records of the patient or of different patients. The system also updates a workflow to optimize the workflow for different kinds of clinical procedures such as PTCA. A customized user interface is provided based on user or hospital department preference and enables user programmable customizable clinical report generation in response to a type of clinical application being performed and user preferences. The system further, provides treatment suggestions and advice in response to patient clinical data and warnings and monitors device and user interface modes and configuration, data formats and automatically adjusts signals (e.g., by filtering) and supports complexity analysis.

The system provides guidelines for display of different kinds of patient information including data from different imaging modality systems (e.g., Ultrasound, X-ray, MRI (magnetic resonance imaging), CT (computer tomography)), patient Vital sign signals (ECG, ICEG, blood pressure, NIBP, SPO2, temperature), patient data from a HIS (hospital information system) and drug treatment related data. The system reduces visualization complexity and patient health status misinterpretation risk and reduces need for non-medical application knowledge and need for clinical workflow alteration. A user friendly interface presents data that tracks clinical workflow progress and comprises different types of patient information. The system interprets continuously acquired patient data providing a health status indication and enables update, creation and modification of a workflow. The system synchronizes different events including administration of treatment, predicts clinical patient specific events, evaluates work performed for timeliness and accuracy, and records changes, and stores records of data change for audit. In one embodiment, the system separates a user interface module (for signal display, reporting) and supports clinical modules (for arrhythmia detection, prediction, prioritization of events, evidence log), and reduces work complexity and error in recording events and mistimed or late data entry.

The system generates chain evidence linking connected events, parameters and medical data for monitoring of medical procedures to dynamically optimize a workflow and executable clinical information application configuration. Chain evidence as used herein comprises a sequence of treatment related tasks, steps, (stages) and corresponding associated monitoring configurations for monitoring real time medical events. A medical device provides a customized clinical platform to record, monitor, track, and interpret patient signals and information and provides a user friendly display interface usable for clinical work analysis and characterization and clinical workflow monitoring.

Figure 1:
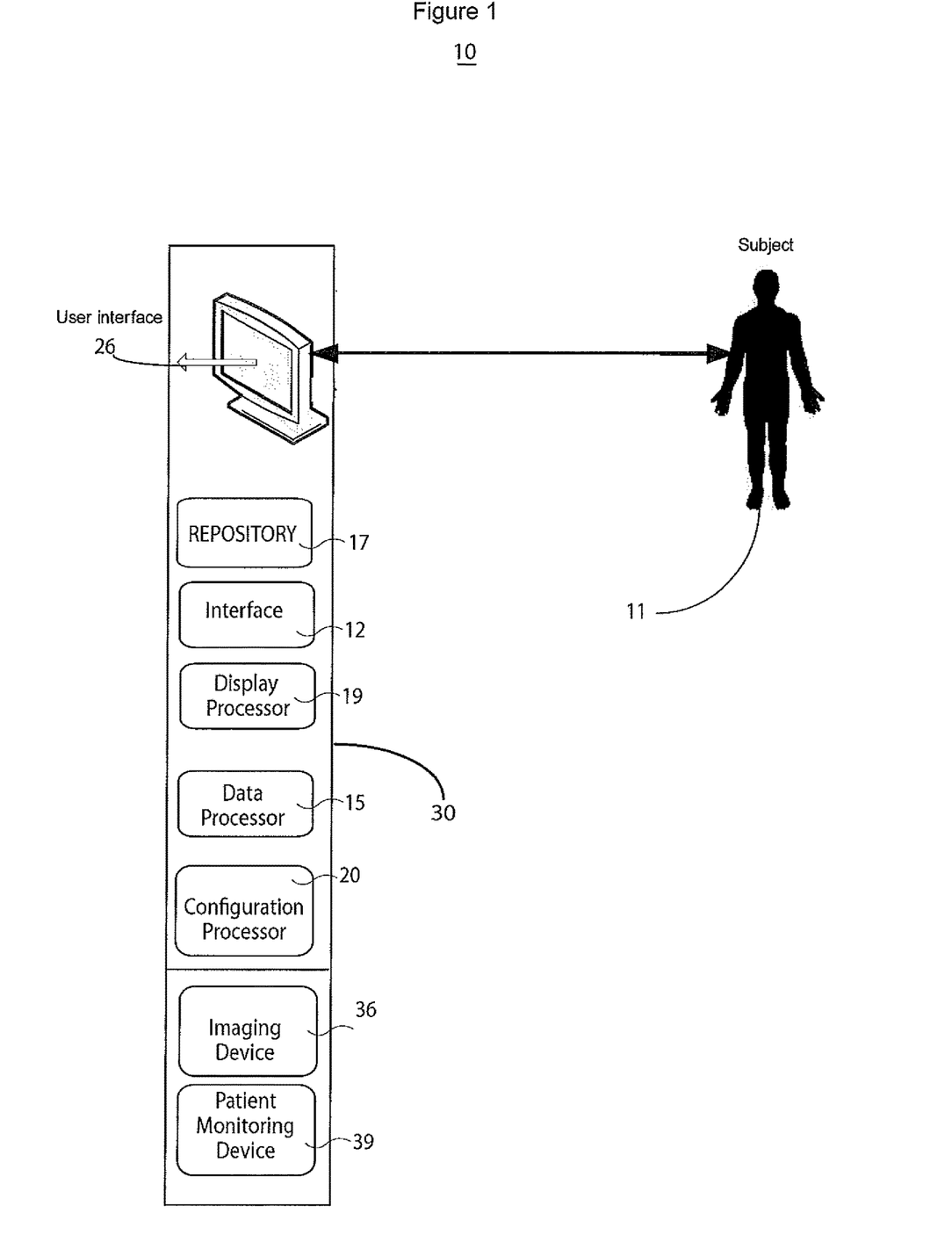
FIG. 1 shows a patient treatment monitoring system, according to invention principles.

FIG. 1 shows patient treatment monitoring system 10. System 10 comprises at least one computer system, workstation, server or other processing device 30 including interface 12, repository 17, display processor 19, data processor 15, configuration processor 20 and a user interface 26. System 10 also includes imaging device 36 and patient monitoring device 39. Interface 12 receives multiple different types of patient medical information including data derived from patient 11 by patient monitoring device 39 and patient medical imaging device 36. Data processor 15 processes the received multiple different types of patient medical information to be suitable for presentation in a display image via user interface 26. Display processor 19 initiates generation of data representing a single composite display image including an image element representing multiple sequentially performed individual stages of a treatment process. The individual stages are associated with corresponding different sets of the received multiple different types of patient medical information. The single composite display image includes multiple image areas for displaying one of the corresponding different sets of the received multiple different types of patient medical information, in response to user selection of a particular stage of the individual stages using the image element. Configuration processor 20 enables a user to configure an individual stage of the multiple sequentially performed individual stages to be associated with a corresponding particular set of the received multiple different types of patient medical information in response to user data entry.

Figure 2:
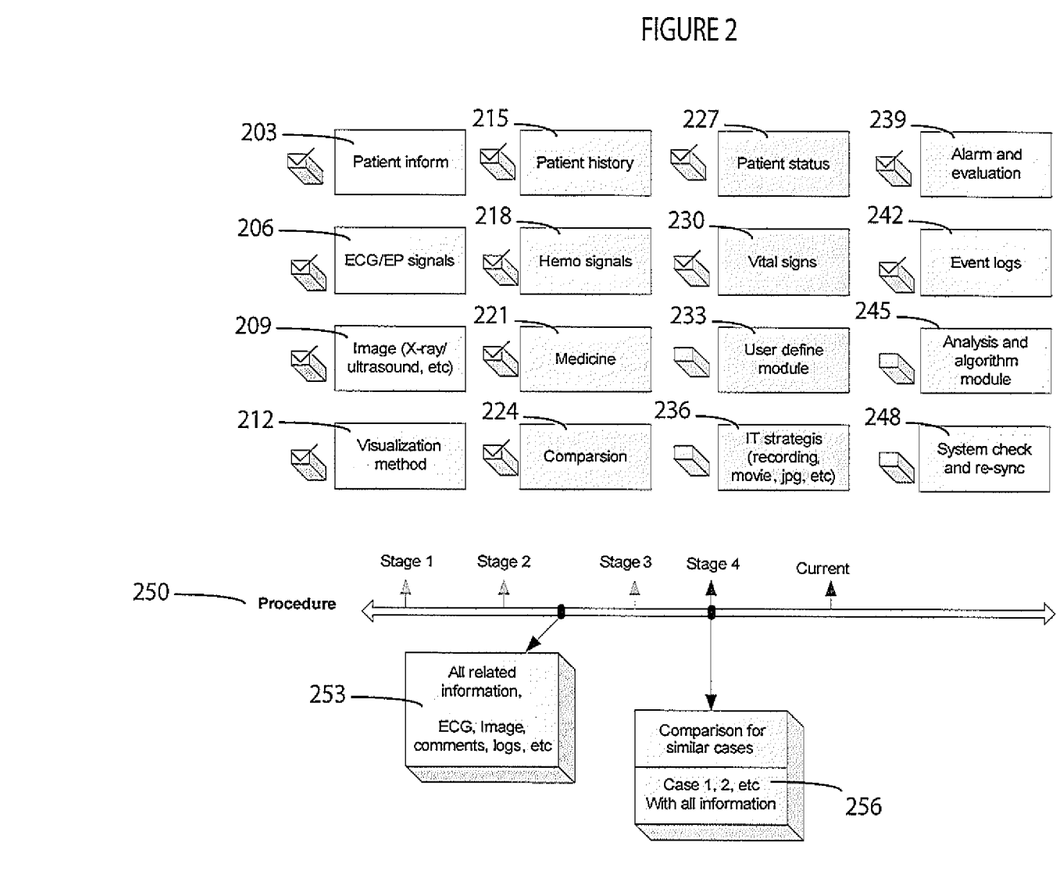
FIG. 2 shows a user interface image supporting configuration of function and information presentation for a clinical workflow and clinical application, according to invention principles.

FIG. 2 shows a graphical user interface image supporting configuration of function and information presentation for a clinical workflow and clinical application. FIG. 2 shows multiple user selectable icons (icons 203-248) enabling a user to configure particular information for presentation in response to user selection of a respective corresponding icon. The user interface image enables a user to configure a patient information and status monitoring user interface image by clinical data priority. The information configured includes data indicating workflow stages, user comments, patient signals, health calculation and warnings, for example. Configuration can be dynamically adaptively modified based on application need and user preference. Clinical procedure and workflow monitoring and tracking involves monitoring and processing different kinds of patient information, signals and data for use in calculations and for presentation in a display. A user configures presentation and processing of patient information 203, EP (including surface ECG and intra-cardiac electrogram) signals 206, X-ray images, Ultrasound images 209, visualization method 212, patient medical history information 215, hemodynamic signals 218, medication administration 221, comparison data, 224, stimulation signals, ablation signals 227, vital sign signals 230, user presentation preferences 233, information presentation data (e.g. still images, MPEG images) 236, alarm thresholds 239, event logs 242, analysis data 245 and system checks and synchronization data 248.

A user via the FIG. 2 image configures patient monitoring and inputs patient information acquired at admission in response to a menu presented upon selection of icon 203 and selects a study and UI-interface for a particular clinical treatment protocol, such as for a blood pressure case and EP (Electrophysiological) case upon selection of icon 212, for example. A user selects measuring signal ranges and warning thresholds in response to selection of icon 239 or uses predetermined default set up data. A configuration of thresholds is automatically adjusted in response to patient medical data or medical user experience, and adjusts NIBP range based on age, respiration rate and heart rate based on age and gender, for example. The different stages in configuration (workflow) are illustrated graphically in time line 250 indicating at what point in a configuration step sequence a particular configuration step is to be performed such as configuration of ECG data 253 between stages 2 and 3 and configuration of data comparison 256 at stage 4.

Figure 3:
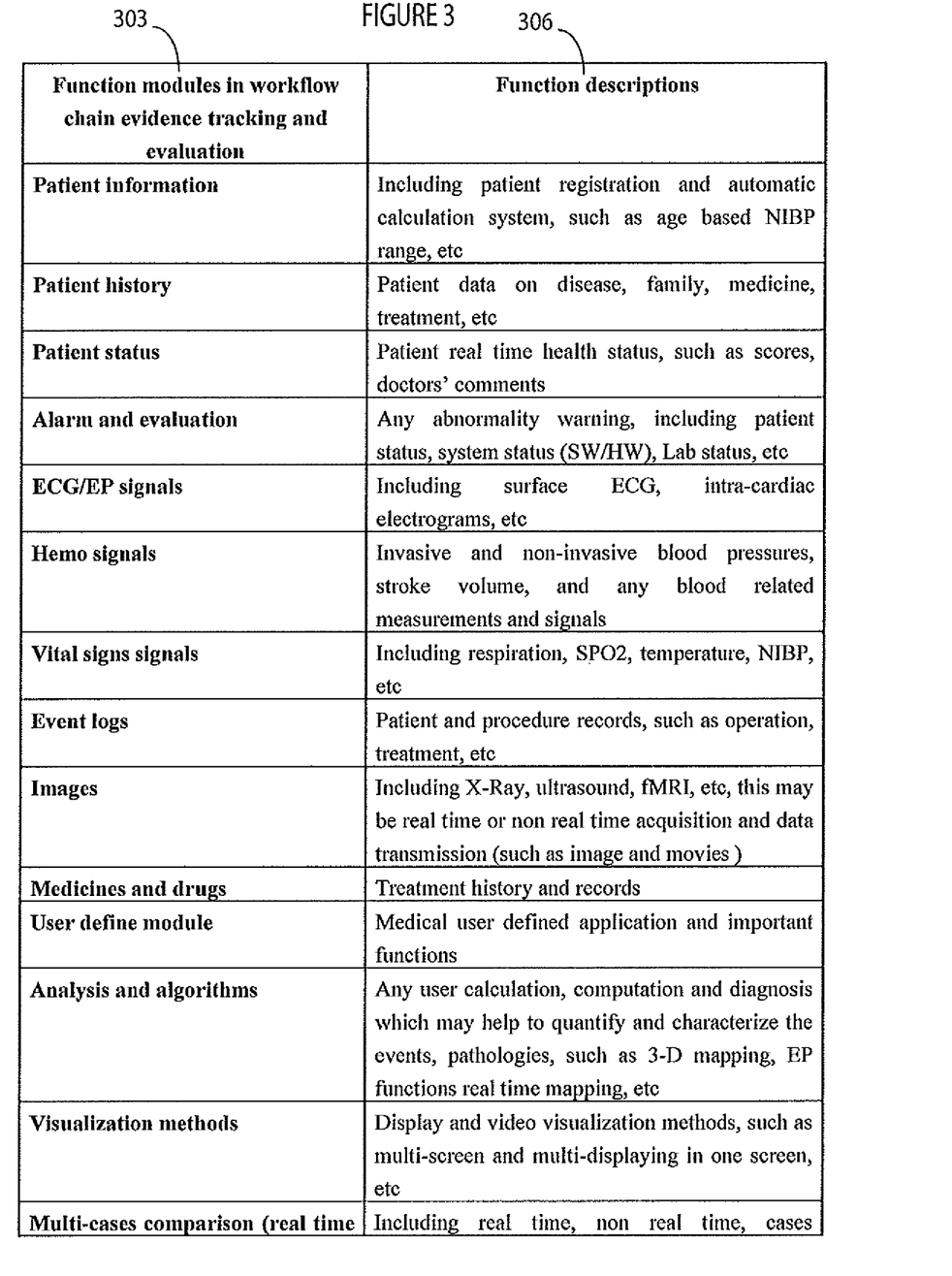
FIG. 3 shows a table of function modules used in UI configuration and work flow setup, according to invention principles.

FIG. 3 shows a table of function modules used in the UI configuration and work flow setup image display of FIG. 2. Individual function modules may be used for corresponding individual different functions, such as comparing drug delivery effects, comparison of ECG ST segment elevation, HW and SW resource changes and consumption rate comparison, for example. Column 303 lists the function modules configured in sequential order from top to bottom and column 306 provides corresponding descriptions of the functions of column 303. The data and signals used by different function modules may come from different medical devices. Hence function configuration includes configuration of an electrical interface and real time data transmission interface between systems and devices.

Figure 4:
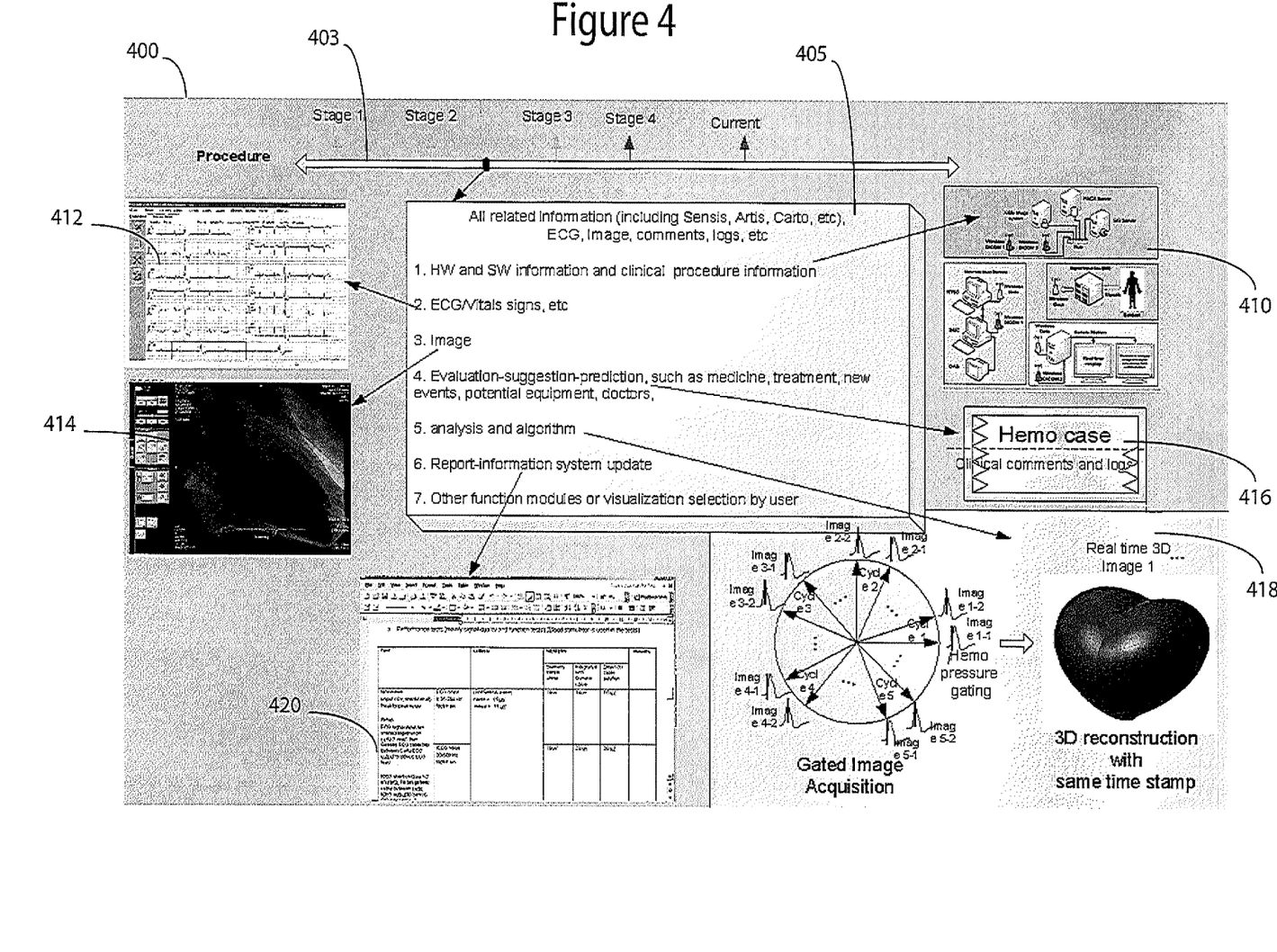
FIG. 4 shows a user interface image for clinical monitoring, tracking and evaluation that tracks treatment stages, successful treatment steps, current steps and next steps, according to invention principles.

FIG. 4 shows user interface image 400 for clinical monitoring, tracking and evaluation that tracks treatment stages, successful treatment steps, current steps and next steps. A clinical procedure and workflow is represented by horizontal timeline and treatment stage bar 403 which helps a user to track progress through multiple treatment stages (stages 1-4) to a current point, as well as to track successful treatment steps, an ongoing procedure and a next procedure. User friendly image 400 advantageously avoids excessive information display in an image window by using a main window 405 presented in the center of image 400. Window 405 comprises a treatment guide and summary linked to timeline bar 403 by a pointer, for example, indicating the corresponding point in treatment stage timeline 403 at which summary window 405 items are performed. The guide and summary window 405 is updated in response to detected changes, in patient medical data available, patient health indicators, system configuration as well as resource consumption. Image windows peripheral to summary window 405, present different real time patient data and derived data provided by analysis as well as information acquired from different resources, such as an imaging system, ECG monitor and user data entry.

The function modules of FIG. 3 that are employed in a workflow, display data in different screens such as multiple screens or different image windows in a composite single screen, big LCD displays, or on one or more different computers. The data displayed is configured in response to predetermined user preferences or data indicating a type of clinical application, treatment or procedure being performed. The function module data displayed in image windows 410, 412, 414, 416, 418 and 420 is selected in response user selection of a particular point in a workflow by selecting a cursor point along slider stage timeline bar 403. For example, in image 400, an ongoing study stage 4 is selected as a user desires to see current information or compare present information with previous information by selecting different time stamp point in the work flow bar. Image window 410 shows hardware and software related system configuration information together with clinical procedure information. Image window 412 presents ECG and vital sign data. Image window 414 presents a medical image, window 416 presents patient diagnosis data, candidate treatment suggestions, medicine data, equipment to be used and physician information. Window 418 shows analysis data and window 420 shows report information and identifies system updates. In another embodiment, a user selects data displayed using a vertical bar, for example. Image 400 also enables user real time parameter control of stimulation channels and ablation points. The individual image windows 410, 412, 414, 416, 418 and 420 may be independent and used for presenting workflow and clinical application data at a selected point in a treatment workflow.

Figure 5:
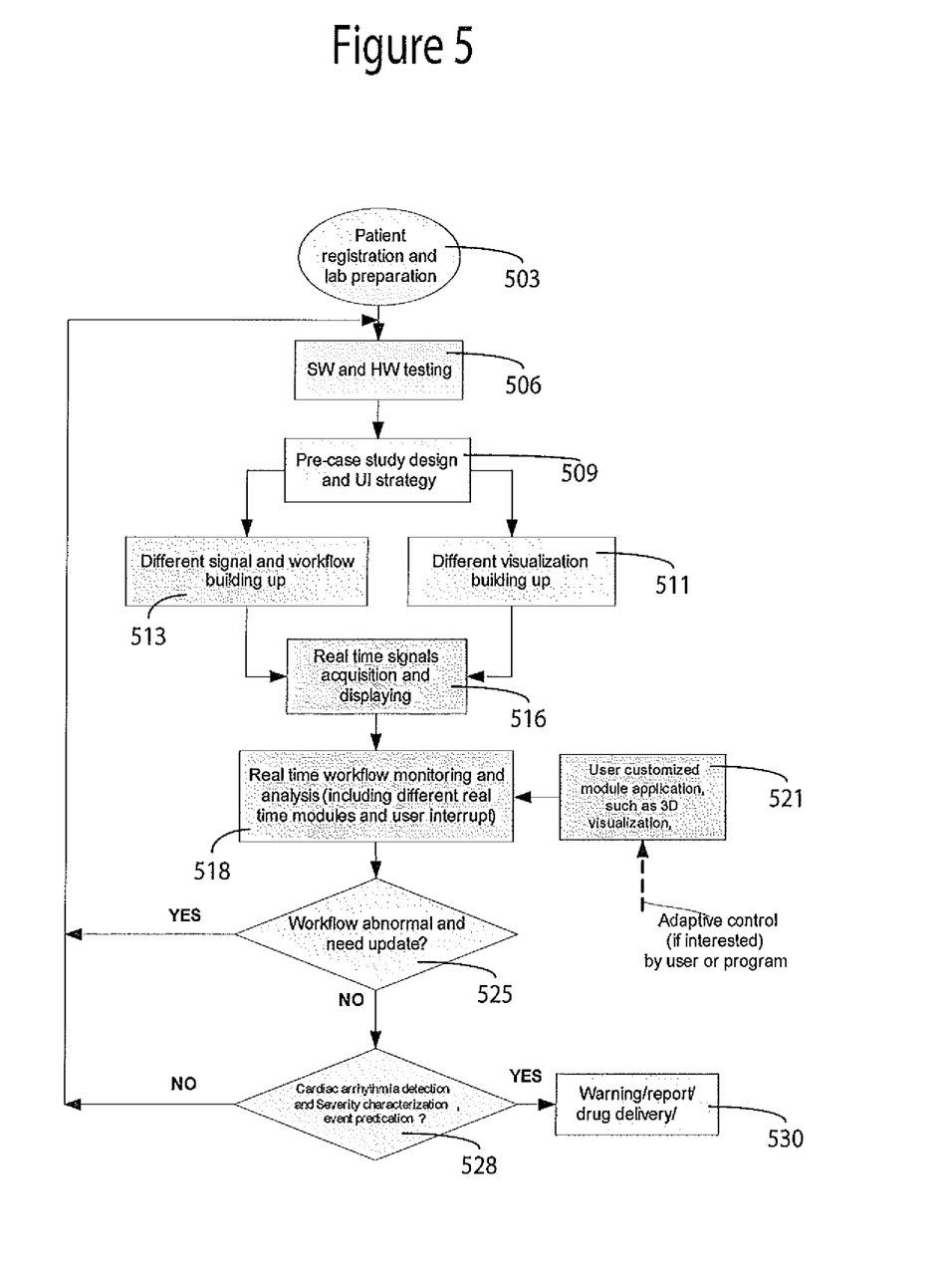
FIG. 5 shows a flowchart of a process for user interface generation and treatment monitoring, according to invention principles.

FIG. 5 shows a flowchart of a process for user interface generation and treatment monitoring. System 10 (FIG. 1) facilitates optimization of a task flow and in one embodiment treats typical recording, analysis and information function modules as individually selectable building blocks, which can be used to build an optimized treatment monitoring task sequence and UI for patient monitoring. System 10 performs hardware and system self test in step 506 following patient registration and catheterization laboratory preparation in step 503. System 10 in step 509 performs processing to select user interface image windows and their content to be presented at the multiple different stages of a treatment workflow. System 10 in step 511 generates data representing the user interface image windows and in step 513 establishes communication links to route signals and data to designated data fields and locations in respective image windows generated in step 511 (e.g., image window 400). In step 516, system 10 performs real time patient signal and data acquisition for display in image windows 410, 412, 414, 416, 418 and 420 of image window 400, for example. System 10 in step 518 performs real time workflow monitoring and analysis using the acquired signals and data in response to user customization and display preferences acquired in step 521 and adaptive system or user control data.

If it is determined in step 525 that the workflow needs an update, steps 506-521 are repeated. If the workflow does not need an update, system 10 in step 528 determines if a cardiac condition (such as arrhythmia) is detected as well as the severity and location of a detected condition in patient tissue and generates a warning in step 530 in response to a detected condition. If no conditions are detected the process of FIG. 5 is iteratively repeated.

Figure 6:
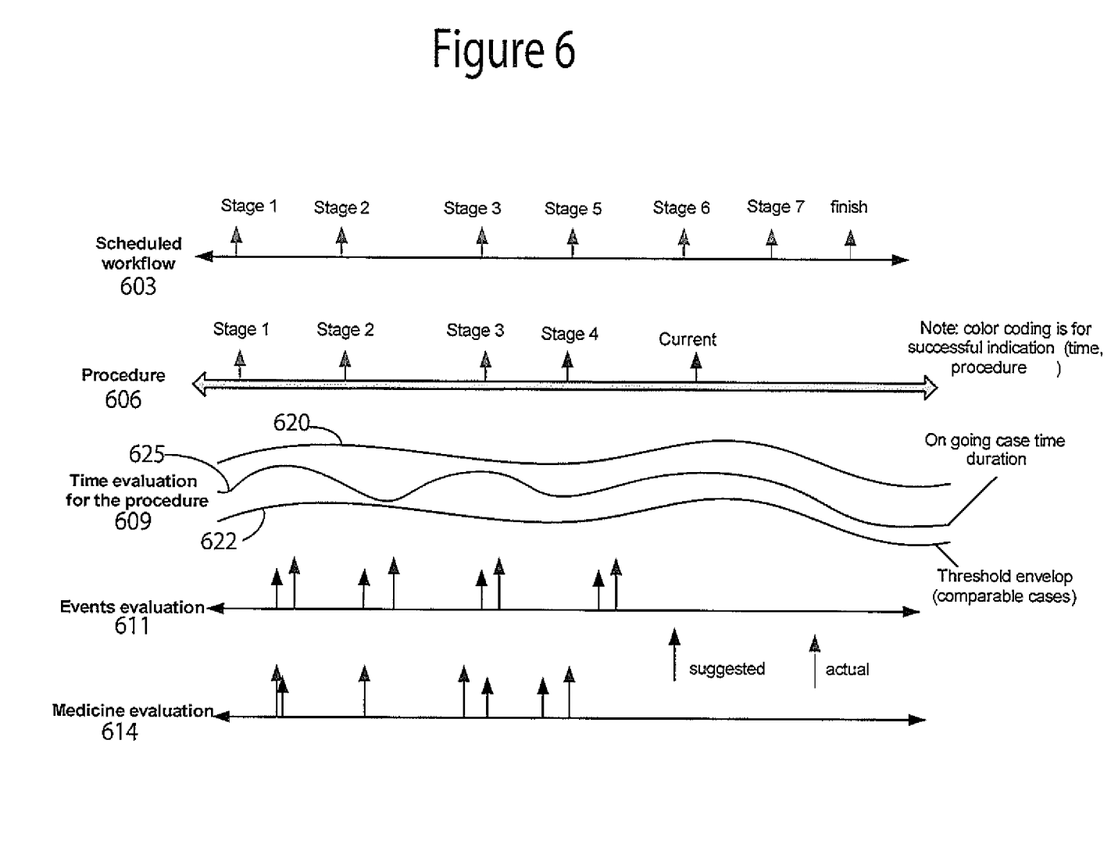
FIG. 6 illustrates monitoring and tracking of a clinical task sequence, according to invention principles.

FIG. 6 illustrates monitoring and tracking of a clinical task sequence by comparison to other similar cases and clinical procedures. System 10 manages a real time currently occurring medical procedure by generating user interface images for managing a task sequence used for clinical assessment and characterization of multiple patients concurrently. The system provides present and past imaging studies of the patient concerned for side by side retrospective comparison, and supports comparison of a patient imaging study with reference images. FIG. 6 shows an example of an ongoing real time procedure (e.g. interventional angiography) and comparison of workflow progress with a reference case having a similar work flow. The comparison is performed by system 10 and comparison data is summarized in a summary window (e.g., window 405 FIG. 4) facilitating user tracking of details of a clinical procedure. System 10 categorizes a workflow of a treatment process into different sequential stages along a timeline 603 so a user is able to track progress of the treatment process using color coded stage completion indicators (e.g., green arrow for success, red for incomplete) along a procedure performance timeline 606 in real time and identifying deviations from a workflow schedule.

The progress of a treatment process is indicated in a time evaluation plot 609 comparing progress in time of a treatment process against upper and lower time duration thresholds 620 and 622 respectively. The thresholds are derived from time duration data of progress of similar cases and procedures. Plot 609 indicates a track of treatment process progress 625 in comparison with upper and lower time duration thresholds 620 and 622. A schedule of suggested clinical evaluation events is shown in timeline 611 together with actual clinical evaluation event occurrences. Similarly, a schedule of suggested medicine evaluation events is shown in timeline 611 together with actual medicine evaluation event occurrences.

The treatment process monitoring of FIG. 6 is applicable to monitoring progress of functions of the different function modules of FIG. 2 in response to user configuration. This is particularly valuable in comparing datasets of the same patient and similar cases to identify abnormality and changes in signals, waveforms and patient data. System 10 compares data derived from a population of patients having similar demographic and medical characteristics as the patient, with the data of the patient, to identify small variation in information, such as electrophysiological signal deviation in an ST segment, image comparison at particular points in a heart cycle, stroke volume calculation variation and drug delivery response time variation. Information indicating how to control and track patient health status and related laboratory resources is derived by comparing image and patient datasets of the same patient derived at different times or by comparing image and patient datasets of the patient with those of different patients, which reduces cost of the laboratory usage, and consumption of processing resources.

Figure 7:
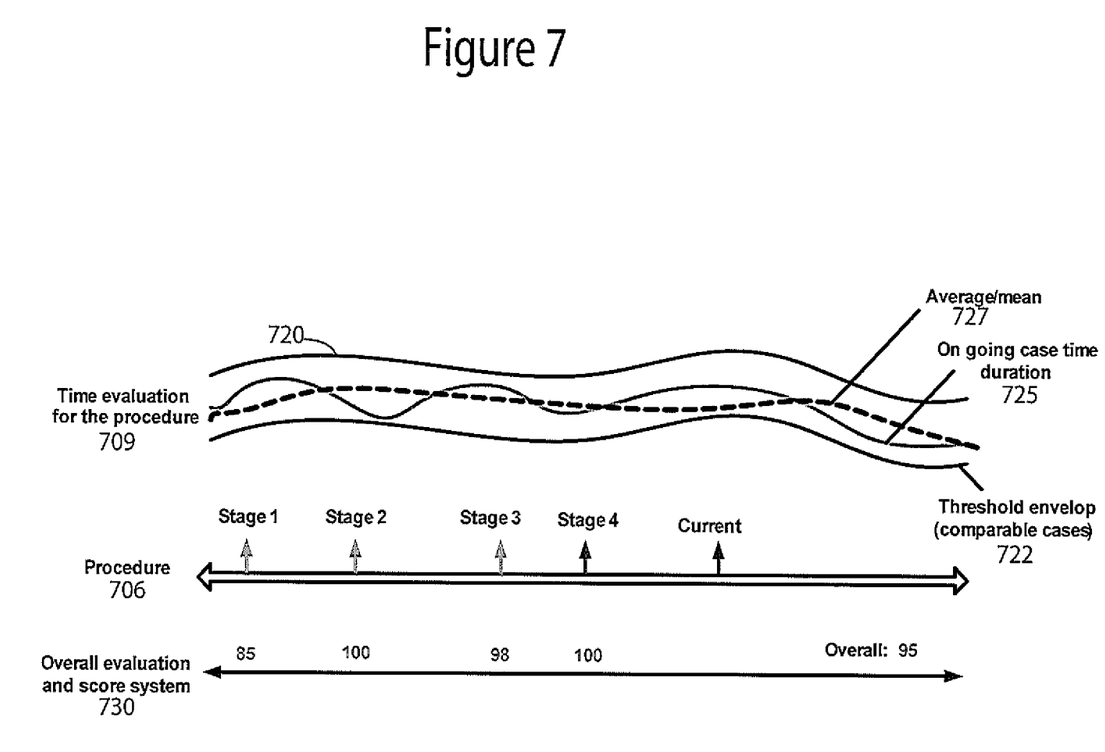
FIG. 7 shows a treatment protocol efficiency monitoring process, according to invention principles.

FIG. 7 illustrates a process for monitoring treatment protocol efficiency by determining a score for evaluation of clinical workflow efficiency. The score facilitates user adjustment of a workflow and user interface to obtain an optimum treatment workflow. The score enables system 10 to automatically adaptively adjust a workflow schedule for retrospective process improvement. The progress of a treatment process is indicated in a time evaluation plot 709 comparing progress in time of a treatment process against upper and lower time duration thresholds 720 and 722 respectively. The thresholds are derived from time duration data of progress of similar cases and procedures. Plot 709 indicates a track of treatment process progress 725 in comparison with upper and lower time duration thresholds 720 and 722 and an average (mean) time 727 for this type of treatment process. The treatment process sequential stages (stages 1, 2, 3, 4) are indicated along a timeline 706 showing progress of the treatment process using color coded stage completion arrows. System 10 determines a score for each stage rating efficiency of individual treatment process workflow stages (e.g. score value 85, 100, 98 and 100 for stages 1-4 respectively). The score value indicates whether a treatment stage is performed on time (score=100), performed earlier than average (e.g., score=95 indicating a 5% greater than an average time to complete a treatment stage) and performed later than average (e.g., score=105 indicating a 5% less than an average time to complete a treatment stage). The score may also reflect success or failure of a treatment stage and overall efficiency of performance of a treatment stage. The higher score of a stage or process, the more efficient is the clinical work and procedure. This is used by system 10 for workflow and treatment improvement.

Figure 8:
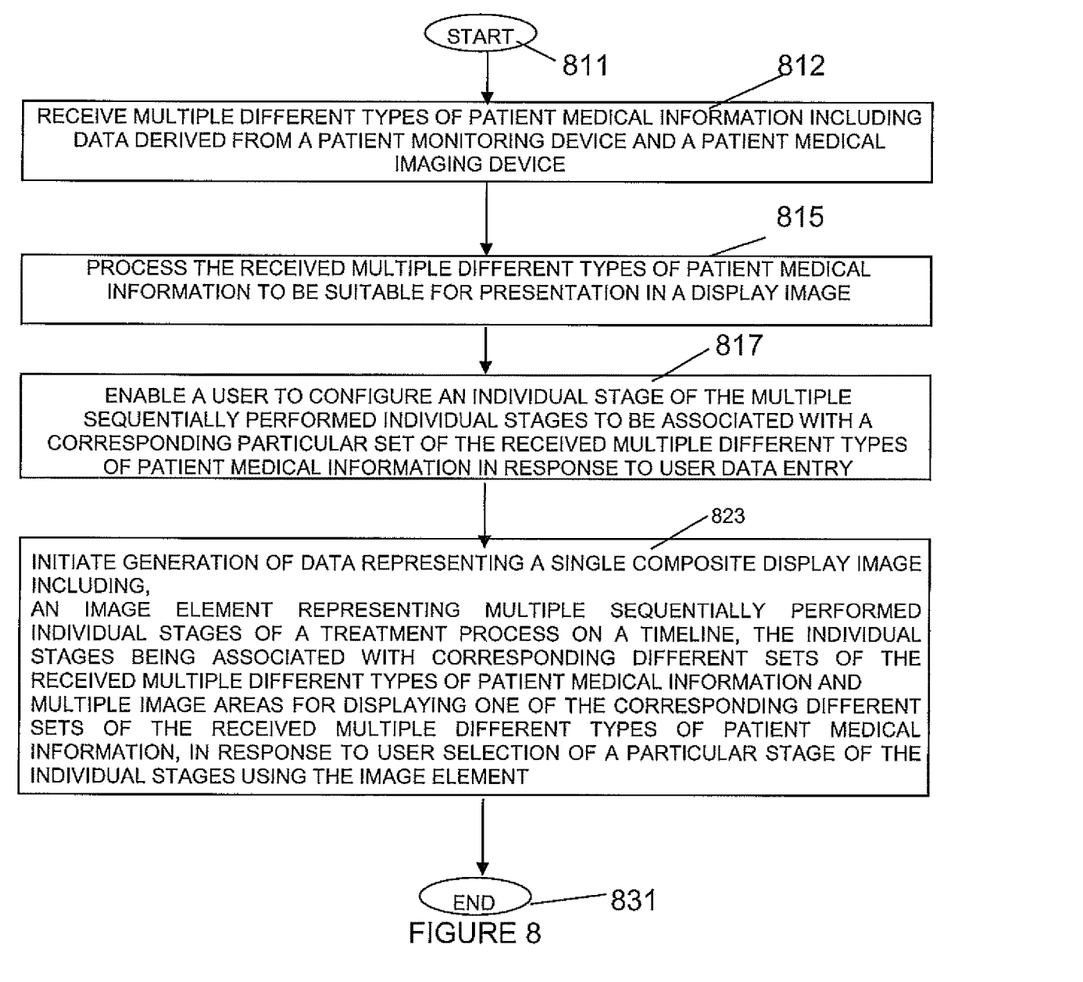
FIG. 8 shows a flowchart of a process used by a patient treatment monitoring system, according to invention principles.

FIG. 8 shows a flowchart of a process used by patient treatment monitoring system 10 (FIG. 1). In step 812 following the start at step 811, interface 12 receives multiple different types of patient medical information including data derived from patient monitoring device 39 and patient medical imaging device 36. Data processor 15 in step 815 processes the received multiple different types of patient medical information to be suitable for presentation in a display image. In step 817 configuration processor 20 enables a user to configure an individual stage of multiple sequentially performed individual stages of a treatment process to be associated with a corresponding particular set of the received multiple different types of patient medical information in response to user data entry.

In step 823 display processor 19 initiates generation of data representing a single composite display image. The single composite display image includes an image element representing multiple sequentially performed individual stages of a treatment process on a timeline. The individual stages are associated with corresponding different sets of the received multiple different types of patient medical information and comprise treatment tasks performed by a healthcare worker. The single composite display image also includes multiple image areas for displaying at least one of the corresponding different sets of the received multiple different types of patient medical information, in response to user selection of a particular stage of the individual stages using the image element. The multiple image areas include a summary image area linked to the timeline by an image element indicating a corresponding point in the timeline associated with items in the summary image area (e.g., when items are performed or activated). The summary image area identifies data presented in the multiple image areas and is updated in response to detected changes in patient medical data available. The multiple image areas include an image area for displaying at least one of, (a) hardware, (b) software and (c) interface configuration data of the patient monitoring device and the patient medical imaging device, (d) patient vital signs provided by the patient monitoring device, (e) a patient medical image provided by the medical imaging device, (f) a suggested treatment or a warning to a physician, (g) indication of administration of a medication to a patient, (h) an overall patient health status indicator, (i) a prediction of a likelihood of success of a next stage of the treatment and (i) a medical report. The multiple image areas also include an image area for displaying at least one of, (i) clinical documentation associated with the selected stage to be competed by a healthcare worker, (ii) results of patient data analysis, (iii) an image 3D reconstruction or an image derived by image data post-processing, (iv) a comparison of patient medical data associated with different stages in response to user selection of multiple particular stages of the individual stages using the image element, (v) data indicating comparison of patient medical data associated with a particular stage with medical data derived from a population of patients having similar demographic characteristics as the patient. The demographic characteristics include at least two of age, height, weight, gender and pregnancy status. The multiple image areas also include an image area for displaying data describing characteristics of the individual stages, data describing characteristics of data presented in remaining areas of the multiple image areas or data indicating a success rate of a particular treatment stage determined based on historical data. The process of FIG. 8 terminates at step 831.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-8 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system in one embodiment generates a composite single user interface image showing a task sequence (bar) comprising multiple treatment steps/stages and enabling a user to select a particular stage and display patient medical data associated with the selected stage in corresponding windows and having a central summary window describing the stages and related data. Further, the processes and applications may, in alternative embodiments, be located on one or more (e.g., distributed) processing devices on a network linking the units of FIG. 1. Any of the functions and steps provided in FIGS. 1-8 may be implemented in hardware, software or a combination of both.

What is claimed is:

1. A patient treatment monitoring system, comprising:
   a configuration processor device for enabling a user to configure function and information presentation;
   an interface for receiving a plurality of different types of patient medical information including data derived from a patient monitoring device and a patient medical imaging device;
   a data processor device for processing the received plurality of different types of patient medical information to be suitable for presentation in a display image; and
   a display processor device for generating, based on user configuration performed via the configuration processor device, data representing a single composite user interface display image including,
      an image element representing a plurality of sequentially performed individual stages of a treatment process on a timeline enabling a user to track, using a color-coded stage completion indicator along a procedure performance timeline, progress of the treatment process in time through the individual treatment stages to a current point and identify progress deviation of the treatment stages based on time duration data of progress of a reference case having a similar workflow, said individual stages being associated with corresponding different sets of the received plurality of different types of patient medical information and
      a plurality of image areas for displaying at least one of said corresponding different sets of the received plurality of different types of patient medical information, in response to user selection of a particular stage of said individual stages using said image element;
   wherein said data processor device provides a score value presented along said timeline for an individual treatment stage indicating whether a treatment stage is performed on time or earlier or later than a reference time for said treatment stage.

2. A system according to claim 1, wherein the configuration processor device further enables the user to configure an individual stage of said plurality of sequentially performed individual stages to be associated with a corresponding particular set of the received plurality of different types of patient medical information in response to user data entry, wherein said image element enables a user to track successful treatment steps, an ongoing procedure and a next procedure.

3. A system according to claim 1, wherein
   said plurality of sequentially performed individual stages of said treatment process comprise treatment tasks performed by a healthcare worker.

4. A system according to claim 1, wherein said plurality of image areas include an image area for displaying at least one of, (a) hardware, (b) software and (c) interface, configuration data of said patient monitoring device and said patient medical imaging device.

5. A system according to claim 1, wherein
   said plurality of image areas include image areas for displaying, (a) patient vital signs provided by said patient monitoring device and (b) a patient medical image provided by said medical imaging device.

6. A system according to claim 1, wherein
   said data processor device provides a score value for an individual treatment stage indicating at least one of, (a) success or failure of a treatment stage and (b) efficiency of performance of a treatment stage, for presentation in said single composite display image and said plurality of image areas include an image area for indicating a suggested treatment or a warning to a physician.

7. A system according to claim 1, wherein said plurality of image areas include an image area for indicating at least one of, (a) indication of administration of a medication to a patient, (b) an overall patient health status indicator and (c) a prediction of a likelihood of success of a next stage of the treatment.

8. A system according to claim 1, wherein said plurality of image areas include an image area for showing a medical report.

9. A system according to claim 1, wherein said plurality of image areas include an image area for showing clinical documentation associated with the selected stage to be completed by a healthcare worker.

10. A system according to claim 1, wherein said plurality of image areas include an image area for showing results of patient data analysis.

11. A system according to claim 1, wherein said plurality of image areas include an image area for showing an image 3D reconstruction or an image derived by image data post-processing.

12. A system according to claim 1, wherein said plurality of image areas include an image area for showing data indicating comparison of patient medical data associated with different stages in response to user selection of a plurality of particular stages of said individual stages using said image element.

13. A system according to claim 1, wherein said plurality of image areas include an image area for showing data indicating comparison of patient medical data associated with a particular stage with medical data derived from a population of patients having similar demographic characteristics as said patient.

14. A system according to claim 12, wherein said demographic characteristics include at least two of age, height, weight, gender and pregnancy status.

15. A system according to claim 1, wherein said plurality of image areas include an image area for showing data describing characteristics of said individual stages.

16. A system according to claim 1, wherein said plurality of image areas include an image area for showing data describing characteristics of data presented in remaining areas of said plurality of image areas.

17. A system according to claim 1, wherein said plurality of image areas include an image area indicating a success rate of a particular treatment stage determined based on historical data.

18. A patient treatment monitoring system, comprising:
an interface for receiving a plurality of different types of patient medical information including data derived from a patient monitoring device and a patient medical imaging device;
a data processor device for processing the received plurality of different types of patient medical information to be suitable for presentation in a display image; and
a display processor device for initiating generation of data representing a single composite display image including,
an image element representing a plurality of sequentially performed individual stages of a treatment process along a timeline enabling a user to track, using a color-coded stage completion indicator along a procedure performance timeline, progress of the treatment process in time through the individual treatment stages to a current point and identify progress deviation of the treatment stages based on time duration data of progress of a reference case having a similar workflow, said individual stages being associated with corresponding different sets of the received plurality of different types of patient medical information and
a plurality of image areas for displaying at least one of said corresponding different sets of the received plurality of different types of patient medical information, in response to user selection of a particular stage of said individual stages using said image element, said at least one of said plurality of image areas including a summary image area identifying data presented in said plurality of image areas and being updated in response to detected changes in patient medical data available;
wherein said data processor device provides a score value presented along said timeline for an individual treatment stage indicating whether a treatment stage is performed on time or earlier or later than a reference time for said treatment stage.

19. A system according to claim 18, wherein said data processor device provides a score value for an individual treatment stage indicating at least one of, (a) a treatment stage is a success or failure and (b) efficiency of performance of a treatment stage and
said summary image area is linked to said timeline by an image element indicating a corresponding point in said timeline at which items in the summary image area are performed.

20. A method for patient treatment monitoring, comprising the activities of:
employing at least one processing device for,
receiving a plurality of different types of patient medical information including data derived from a patient monitoring device and a patient medical imaging device;
processing the received plurality of different types of patient medical information to be suitable for presentation in a display image; and
initiating generation of data representing a single composite display image including,
an image element representing a plurality of sequentially performed individual stages of a treatment process on a timeline enabling a user to track, using a color-coded stage completion indicator along a procedure performance timeline, progress of the treatment process in time through the individual treatment stages to a current point and identify progress deviation of the treatment stages based on time duration data of progress of a reference case having a similar workflow, said individual stages being associated with corresponding different sets of the received plurality of different types of patient medical information;
a plurality of image areas for displaying at least one of said corresponding different sets of the received plurality of different types of patient medical information, in response to user selection of a particular stage of said individual stages using said image element; and
a score value for an individual treatment stage indicating whether a treatment stage is performed on time or earlier or later than a reference time for said treatment stage.

21. A method according to claim 20, including the activity of providing a score value for an individual treatment stage indicating at least one of, (a) a treatment stage is a success or failure and (b) efficiency of performance of a treatment stage and wherein
    said plurality of image areas include a summary image area is linked to said timeline by an image element indicating a corresponding point in said timeline at which items in the summary image area are performed.

* * * * *